United States Patent
Trede et al.

(10) Patent No.: US 9,478,020 B2
(45) Date of Patent: Oct. 25, 2016

(54) METHOD FOR ANALYSING THE EFFECT OF A TEST SUBSTANCE ON BIOLOGICAL AND/OR BIOCHEMICAL SAMPLES

(75) Inventors: Dennis Trede, Bremen (DE); Peter Maass, Bremen (DE); Hartwig Preckel, Hamburg (DE)

(73) Assignee: PerkinElmer Cellular Technologies Germany GmbH, Hamburg (DE)

( * ) Notice: Subject to any disclaimer, the term of this patent is extended or adjusted under 35 U.S.C. 154(b) by 40 days.

(21) Appl. No.: 12/991,236

(22) PCT Filed: Apr. 29, 2009

(86) PCT No.: PCT/EP2009/055187
§ 371 (c)(1),
(2), (4) Date: Dec. 17, 2010

(87) PCT Pub. No.: WO2009/135790
PCT Pub. Date: Nov. 12, 2009

(65) Prior Publication Data
US 2011/0098198 A1 Apr. 28, 2011

(30) Foreign Application Priority Data
May 7, 2008 (EP) .................................... 08155784

(51) Int. Cl.
| | | |
|---|---|---|
| *G01N 33/48* | (2006.01) | |
| *G06T 7/00* | (2006.01) | |
| *G06F 19/28* | (2011.01) | |
| *G06G 7/58* | (2006.01) | |
| *G06F 19/24* | (2011.01) | |

(52) U.S. Cl.
CPC .............. *G06T 7/0012* (2013.01); *G06F 19/28* (2013.01); *G06F 19/24* (2013.01); *G06T 2207/30072* (2013.01)

(58) Field of Classification Search
CPC .............................. G06F 19/02; G06F 19/248
See application file for complete search history.

(56) References Cited

U.S. PATENT DOCUMENTS

| | | | |
|---|---|---|---|
| 2009/0075360 A1* | 3/2009 | Ho et al. ................. | 435/284.1 |
| 2009/0204374 A1* | 8/2009 | Hill et al. ................ | 703/2 |
| 2011/0008803 A1* | 1/2011 | Stockwell ............... | 435/7.23 |

FOREIGN PATENT DOCUMENTS

WO WO 2006/063216 6/2006

OTHER PUBLICATIONS

Wu et al.; "*Experimental Designs for Optimization of the Image a Analysis Process for cDNA Microarrays*"; Chemometrics and Intellegent Laboratory Systems; 2005; pp. 175-184.
Zhang et al.; "*A Simple Statistical Parameter for Use in Evaluation and Validation of High Throughput Screening Assays*"; Journal of Biomolecular Screening; Nov. 2, 1999; pp. 67-73.
Barlow et al.; "*Hill Coefficients and the Logistic Equation*"; TiPS; Nov. 1989; pp. 1-2.
International Search Report dated Jul. 10, 2009 for PCT/EP2009/055187, 3 pages.

* cited by examiner

*Primary Examiner* — Eric S Dejong
(74) *Attorney, Agent, or Firm* — Ohlandt, Greeley, Ruggiero & Perle, LLP

(57) ABSTRACT

Disclosed are methods for analyzing the effect of a test substance on biological and/or biochemical samples in which a plurality of samples, each comprising a known concentration of the test substance in at least three different concentrations, are used to obtain measurements which provide raw data. An evaluation rule utilizes the raw data of the sample determining the effect of the test substance, at the particular concentration, on the sample. The evaluation rule is influenced by at least one control parameter, and at least one starting value for the at least one control parameter is determined. The raw data is evaluated and correspondence between the determined activities and a functional model resulting from theoretical considerations yields a dose/effect curve describing the dependence of the activities on the concentration of the test substance. The steps are modified and repeated until an abort criterion has been reached.

10 Claims, 9 Drawing Sheets

$q_1 = 0.8 \mapsto 0.6485$
$q_2 = 0.9 \mapsto 1.0$
$\mu_1 = 1.0 \mapsto 0.46363$
$\mu_2 = 1.0 \mapsto 0.45558$
$\lambda = 1.0 \mapsto 1.2098$
Zone 1:
$\quad 0 \mapsto 2.5542$
$\quad 4 \mapsto 3.6914$
Zone 2:
$\quad 7 \mapsto 4.7645$
$\quad 13 \mapsto 11.9581$
Fig.8
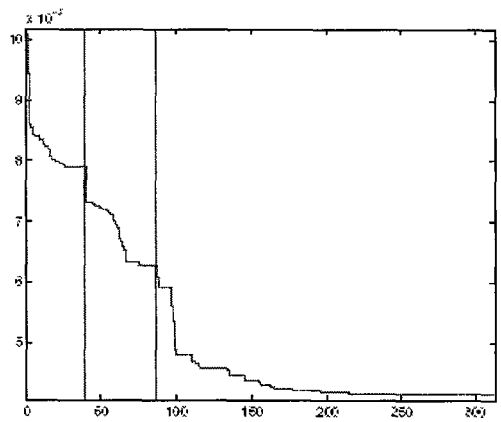
Fig.9
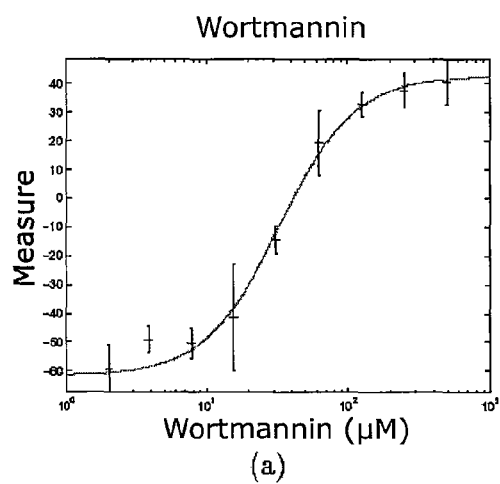
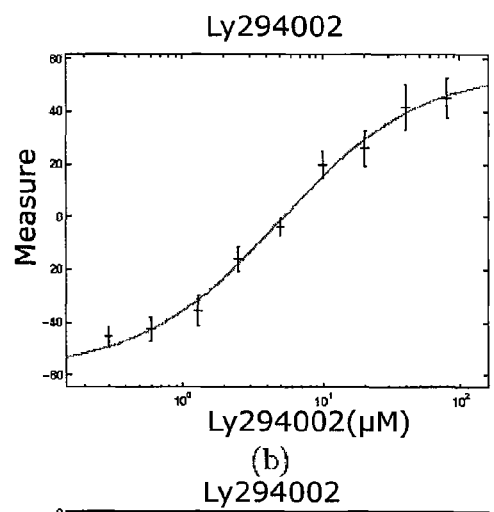
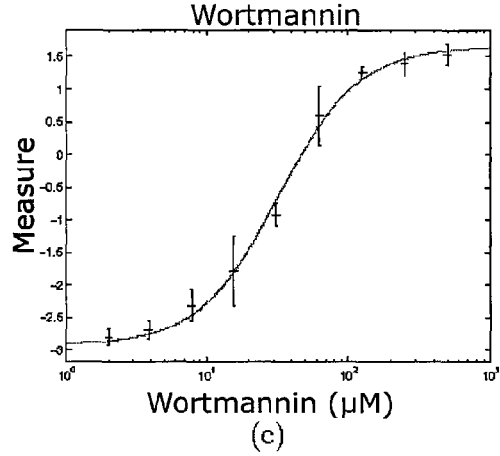
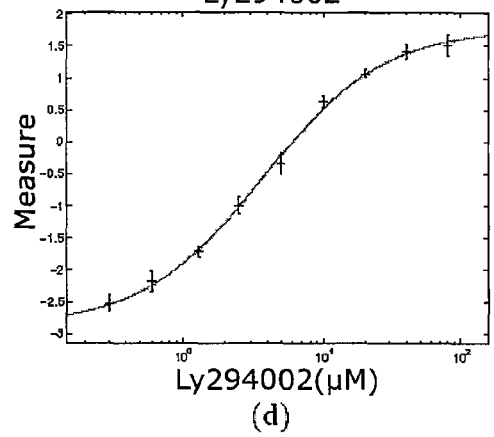
Fig.10

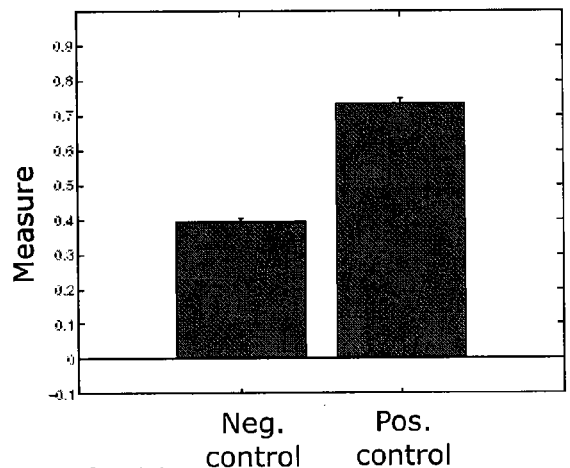
Fig.11
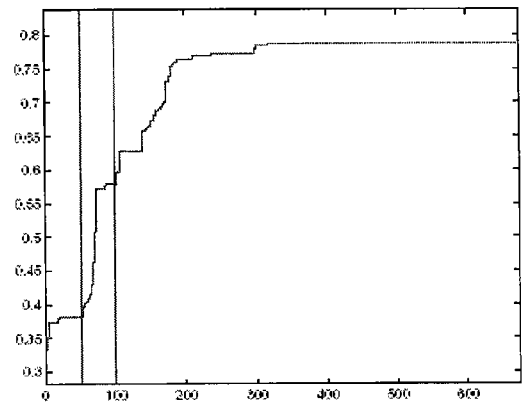
Fig.12
$q_1 = 0.8 \mapsto 0.13467$
$q_2 = 0.9 \mapsto 0.43262$
$\mu_1 = 1.0 \mapsto 0.28786$
$\mu_2 = 1.0 \mapsto 0.24944$
$\lambda = 1.0 \mapsto 0.99737$
Zone 1:
$\quad 0 \mapsto 0.048674$
$\quad 4 \mapsto 3.9627$
Zone 2:
$\quad 7 \mapsto 7.0055$
$\quad 13 \mapsto 12.2013$
Fig.13
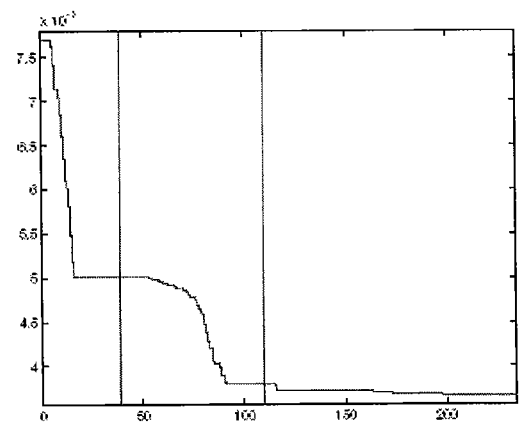
Fig.14

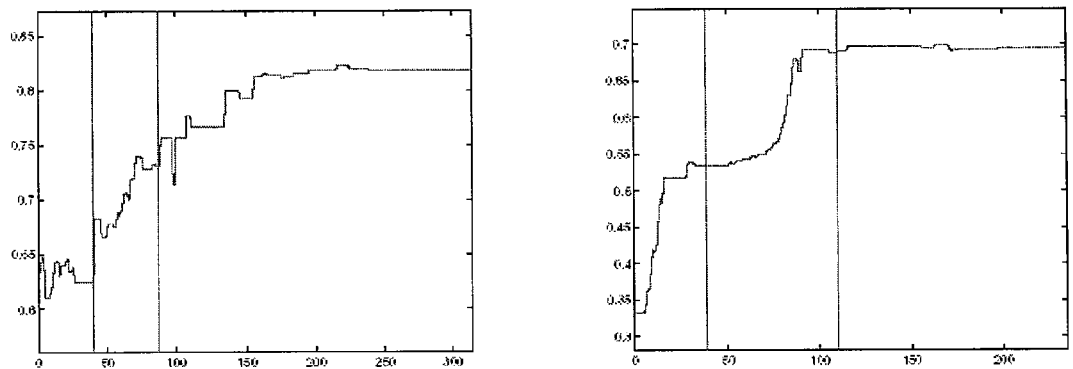
Fig.17
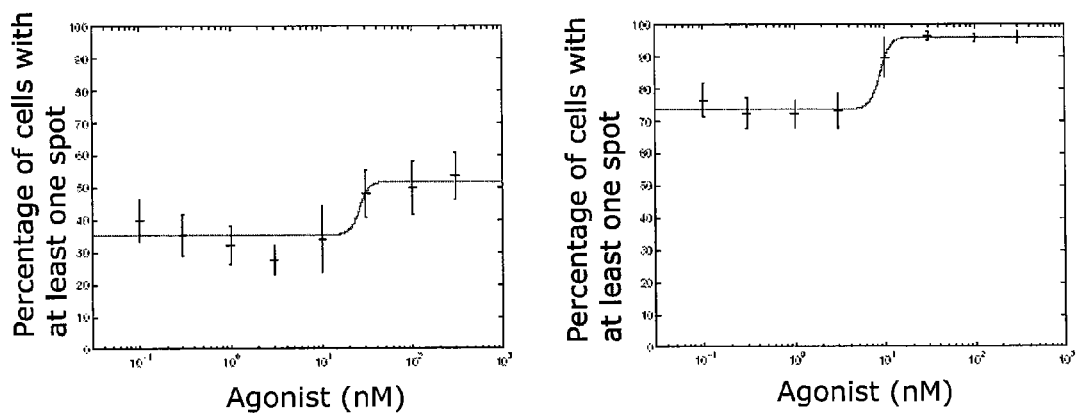
Fig.18
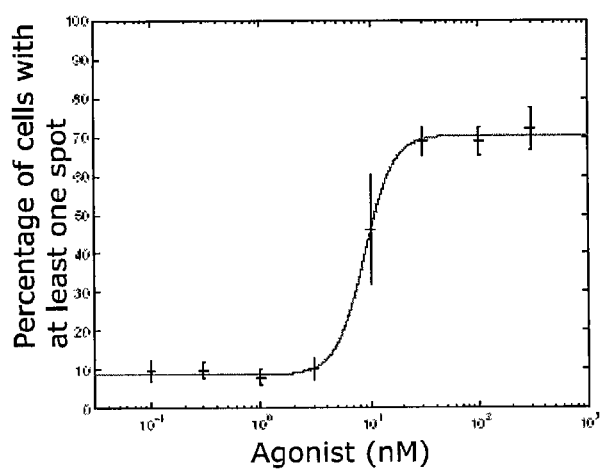
Fig.19
Zone 1:
    -5.0 ⟼ -8.0685
Zone 2:
    5.0 ⟼ 9.4430
SpotMinimumDistance:
    3.0 ⟼ 16.6058
SpotPeakRadius:
    0.0 ⟼ 1.9822
SpotReferenceRadius:
    3.0 ⟼ 61.9845
SpotMinimumContrast:
    0.3 ⟼ 0.4448
SpotMinimumToCellIntensity:
    1.0 ⟼ 0.0
Fig.20

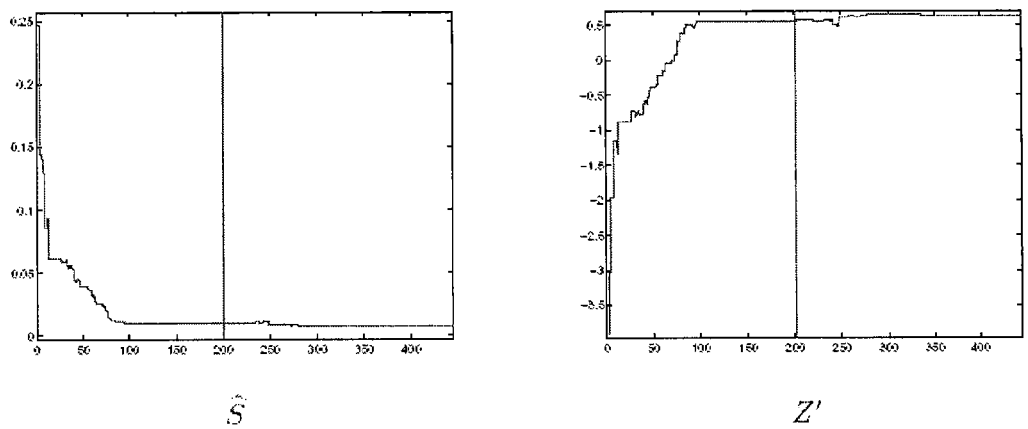
Fig.21
Fig.22
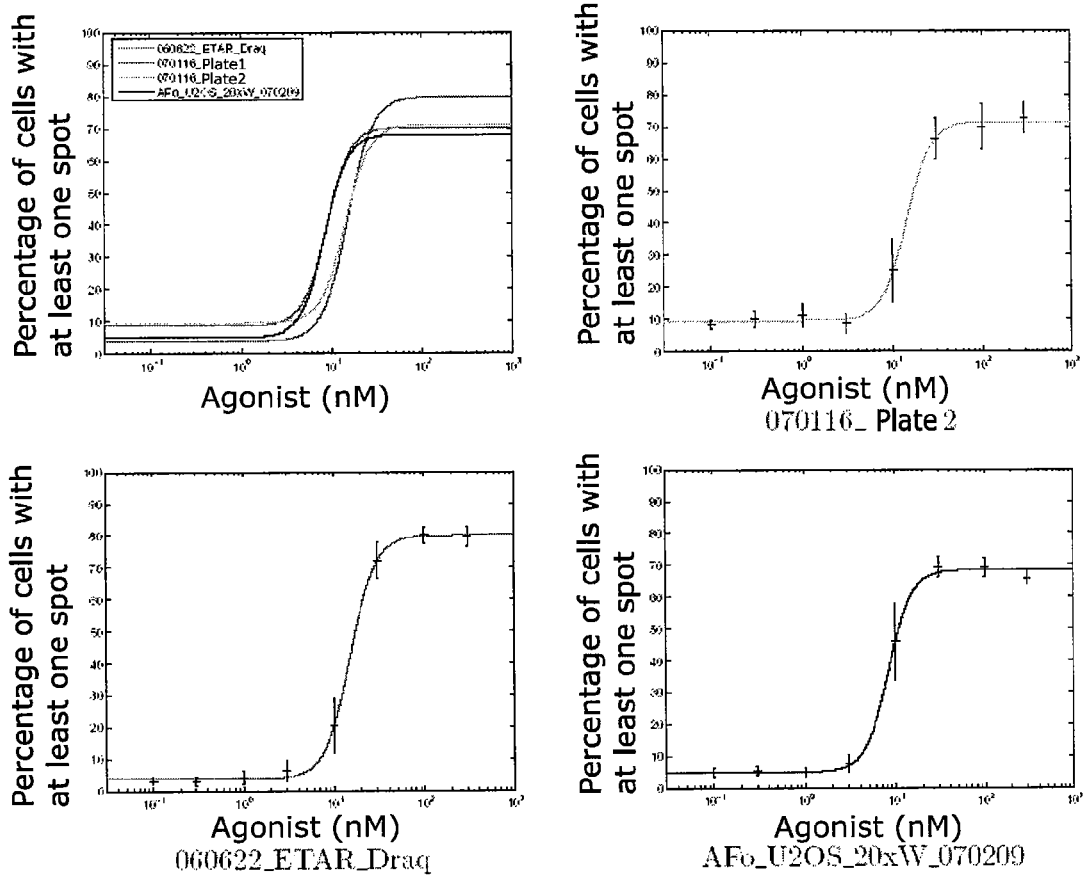
Fig.23

Zone 1:
 -5.0 ⟼ -19.4999
Zone 2:
 5.0 ⟼ 19.5236
SpotMinimumDistance:
 3.0 ⟼ 11.5618
SpotPeakRadius:
 0.0 ⟼ 3.0686

SpotReferenceRadius:
 3.0 ⟼ 64.6338
SpotMinimumContrast:
 0.3 ⟼ 0.2615
SpotMinimumToCellIntensity:
 1.0 ⟼ 0.4173

METHOD FOR ANALYSING THE EFFECT OF A TEST SUBSTANCE ON BIOLOGICAL AND/OR BIOCHEMICAL SAMPLES

BACKGROUND

1. Field of the Disclosure

The disclosure relates to a method for analysing the effect of a test substance on biological and/or biochemical samples, particularly on samples comprising living cells. The method of the disclosure is particularly suited for the characterizing of test substances in HTS or HCS.

2. Discussion of the Background Art

High-throughput screening (HTS) and high-content screening (HCS) are methods used in the pharmaceutical and biotech industry in an effort to search for new active agents against hard-to-treat illnesses. In these methods, biochemical and/or biological samples which particularly comprise living cells, are treated with test substances such as e.g. synthetic substances, and the interaction will be analysed. "High-throughput screening" refers to the very high data throughput of the method herein (testing performed on more than 100,000 substances per day), and "high-content screening" refers to the high—particularly cellular—resolution of the signals which are to be analysed.

For performing an analysis of the effect of a test substance on a sample, particularly a cellular sample, there will first be provided a plurality of samples. These samples each comprise a known concentration of the test substance. Subsequently, measurements will be performed, particularly in high-throughput screening, wherein the samples will be e.g. illuminated by visible or non-visible light of defined wavelengths or wavelength ranges, and the radiation which is emitted by the sample, particularly due to luminescence, will be detected. In this manner, a plurality of raw data are captured per sample. Thereafter, normally, a segmentation of the obtained raw data is carried out with the aid of known image processing routines. In the process, there is performed particularly a segmentation of the cells and/or subcellular structures. Then, for the interactions to examined, an evaluation rule will be procured. From the raw data of the individual sample, a respective activity value will be obtained by use of the evaluation rule or a modelization. Said activity value describes the effect of the test substance at the present concentration. The procured evaluation rule is influenced by at least one control or model parameter. Thus, said at least one control parameter will have to be set. Since the process of setting the respective control parameters is extremely complex, this can be performed, in state-of-the-art analysis methods, only by a skilled specialist because the settings of the control parameters are normally based also on empirical values and on biological argumentation. With the aid of the so-called evaluation rule, the image data will be evaluated, and, for doses $d_i$, $i=1, \ldots, n$, measurements $m_i$ will be obtained which quantize the interactions in the image i. In the next step, these data $$(d_i, m_i)_{i=1}^{n}$$

will be statistically evaluated. The statistical evaluation of the data includes e.g. the computation of the Z'-value: a statistical indicator for high-throughput screening that is an evaluation of the quality. A further statistical indicator is the dose/effect curve which represents the relation between the substance activity and the dose of the substance.

Often, the quality of the analysis depends on control parameters which have to be suitably selected. Such control parameters can be, e.g., threshold values or statistical values of the model. These will customarily be set by hand on the basis of empirical values. Further, the applicant owns a parameter scanner which is operative to search for a good setting within a finite discrete subset—which must be indicated—of all possible control parameters. The search for suitable control parameters is very bothersome.

It is an object of the disclosure, in a method for analysing the effect of a test substance on biological and/or biochemical samples, to improve the setting of the control parameters so as to accomplish an improvement of the analysis results. Particularly, it is a further object of the disclosure to provide a method of the above type wherein an automatic, preferably optimized setting of the control parameters is performed.

SUMMARY

The above object is achieved by a method for analysing the effect of a test substance on biological and/or biochemical samples, particularly on samples comprising living cells, said method comprising the following steps:

a. providing a plurality of samples each comprising a known concentration of the test substance, wherein at least three different concentrations of the test substance are used;

b. performing measurements which provide a plurality of raw data items per sample;

c. providing an evaluation rule which uses the raw data of a sample to determine a respective activity value describing the effect of the test substance at the present concentration, the evaluation rule being influenced by at least one control parameter;

d. determining at least one starting value for the at least one control parameter;

e. evaluating the raw data using the evaluation rule;

f. determining a measure of the correspondence between the determined activities and a functional model which results from theoretical considerations and has a dose/effect curve describing the dependence of the activities on the concentration;

g. modifying at least one control parameter and repeating said steps e. to g. as long as an abort criterion has not been reached.

Thus, the analysis method of the disclosure is based on the provision of a parameter optimization which is suited particularly for the high-content analysis in high-throughput screening. Herein, according to the disclosure, the control parameters will be set with the aid of the—particularly statistical—evaluation of the raw data by means of the evaluation rules. By such a reference, an improvement will be achieved in an iterative manner. According to the disclosure, this is possible preferably without the need to preset the parameters on the basis of biological substantiations. Thus, according to the disclosure, the setting does not necessarily have to be carried out by a specialist having corresponding detailed skills. This is to say that, according to the disclosure, the setting of the control parameters with the aid of the results of the—particularly statistical—evaluation of the raw data will be performed iteratively.

Through this iteration, one can accomplish an improvement of the existing control parameters and, respectively, of the control parameters used for analysis.

Particularly, the raw data used for obtaining the activity values therefrom are image data. Preferably, the image data comprise also microscopic image data. The image data are generated particularly by illuminating or irradiating the sample, whereby the sample will be excited to produce luminescence, particularly fluorescence. For this purpose, the sample and/or the test substance preferably should have been marked by dye markers or the like. It is particularly preferred that a plurality of measurements are performed per sample. For instance, measurement will be performed using a plurality of different excitation and/or emission wavelengths. Further, it is possible to provide different polarizations in the excitation radiation.

It is particularly preferred to subject a sample to a plurality of different measurements in different object planes and/or at different successive times so as to obtain information on the three-dimensional structure and/or on temporal changes of the sample. In this case, it is especially preferred that the raw data obtained from a plurality of measurements per sample will each time be evaluated together by use of the evaluation rule so as to obtain an activation value. In this manner, the activity of the test substance can be gathered from the temporal development of the effect of the substance on the sample and/or from the influence of the substance on the three-dimensional structure of the sample.

According to the disclosure, a plurality of samples will be provided. This can be performed, as commonly practiced in high-throughput screening, by arranging the samples in microtitration plates. Preferably, the samples comprise three to thirty and, more preferably, five to fifteen different concentrations. Thus, the individual samples preferably comprise the same concentration of the sample substance which is to be examined, particularly the same quantity of cell suspension while, then, different concentrations of test substance will be added. In this regard, it is preferred that a plurality of samples with an identical concentration of test substance will be procured for use. These samples represent the same point on the dose/effect curve. In this manner, it is possible, by use of statistical average values, to reduce influences of wrong measurements or wrong concentrations, for instance.

Preferably, each sample, as arranged e.g. on a microtitration plate, comprises the same concentration of the sample substance. This is achieved e.g. by dispensing an identical quantity of a cell suspension into each well. In this case, it can be assumed with high probability that all wells contain identical numbers of cells or numbers of cells in the same order of magnitude.

A preferred variant of the analysis method provides that, for each sample, the measurement is performed in a plurality of spatial partial regions.

Preferably, the evaluation rule includes steps for segmentation, object detection, determination of geometric values, brightness values, texture parameters of the total image and/or segments/objects detected in the image, the number of objects, the relative position of objects in relation to each other (e.g. spots in cells), the relation of brightness degrees in different measurement channels (different markers), statistical values derived from the above mentioned values, e.g. quantiles, the percentage of objects/cells having a specific property, properties of subsets (sub-populations) of objects etc.

The control parameters having an influence on the evaluation rule preferably comprise at least one or several of the following control parameters: brightness thresholds, value thresholds, position and size of masks for integration or object search, as well as threshold values and/or weighting factors for the above mentioned values or combinations of the values.

Preferably, the functional model which is based on theoretical considerations comprises the Hill equation for the dose/effect curve.

An essential aspect of the analysis method of the disclosure resides in determining the measure of coincidence between the detected activities and the functional model for the dose/effect curve. Preferably, there will be performed a numerical adaptation of the functional model to the detected activities. Further, it is preferred to determine a normalized average square deviation of the detected activities from the adapted functional model. In this manner, it is possible, by performing the iteration steps of the disclosure, to select good and preferably optimal control parameters.

Preferably, the iteration process will be aborted in dependence on abort criterion. The abort criterion can be e.g. the reaching of a maximum number of iteration steps. Preferably, the abort criterion will consist of one or several of the criteria mentioned hereunder:

falling short of a previously determined normalized average square deviation, and/or falling short of a previously determined minimum change from step to steps, and/or reaching a maximum number of iteration steps.

Further, it is preferred that the method is performed in a plurality of stages. First, in this case, a first group of control parameters will be improved or optimized by use of the method of the disclosure. This will be performed until the abort criterion is reached. Then, an improvement/optimization of a second group of control parameters will be performed. This will continue until a second abort criterion is reached. Optionally, also still further—i.e. third, fourth etc.—groups of control parameters can be provided and be improved/optimized as provided by the disclosure.

The analysis method of the disclosure particularly has the advantage of being applicable without requiring specialized knowledge or specially trained personnel for adaptation of the control parameters. Thus, particularly in its preferred embodiment, the analysis method is user-independent. The automation of the selecting of the control parameters which is rendered possible by the disclosure, will save considerable time.

In the analysis method of the disclosure, use is made of the data of a dose/effect curve of a test substance for parameter adaptation. By using a functional model based on theoretical considerations and involving a dose/effect curve describing the dependence of the activities on the concentration, the deviation of the detected activities during the optimization steps will be minimized. As soon as the dose/effect behavior acting on the test substance has been optimized as provided by the disclosure, the analysis will provide good results for a large range of variations and for other impounds.

BRIEF DESCRIPTION OF THE DRAWINGS

The inventive optimization of the control parameters will be explained in greater detail hereunder by way of an example. In the accompanying drawings, the following is shown.

DETAILED DESCRIPTION OF THE PREFERRED EMBODIMENT

Figure 1:
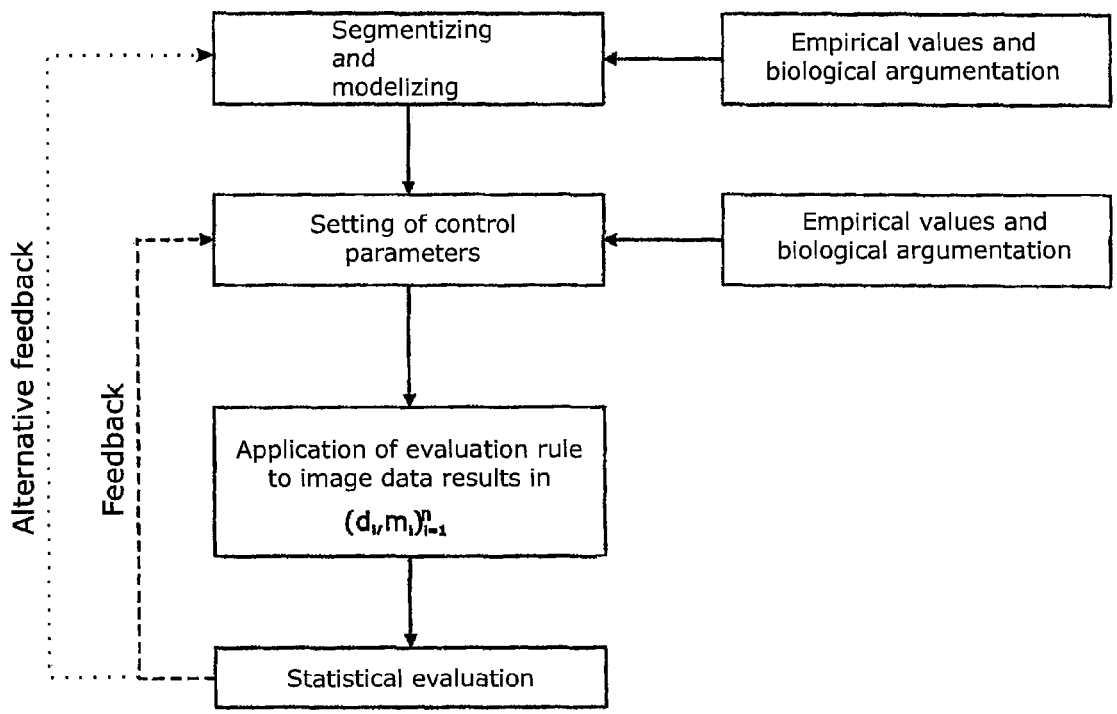
FIG. 1 a schematic representation of the sequence of the individual steps of the method, FIG. 2 a diagram of a normalization of a dose/effect curve, FIG. 3 exemplary histograms of the membrane masks, (a) stimulated cell, (b) unstimulated cell, FIG. 4 exemplary histograms of the cytoplasm masks, (a) stimulated cell, (b) unstimulated cell, FIG. 5 the relation between quantiles $q_1$ and $q_2$ and the Z'-value, Akt3 assay, Whatman dataset, FIG. 6 the development of the Z'-value, Akt3 assay, Whatman dataset, FIG. 7 control well values after Z'-optimization, Akt3 assay, Whatman dataset, FIG. 8 Ŝ-optimized parameters, Akt3 assay, Whatman dataset, FIG. 9 the development of the Ŝ-value, Akt3 assay, Whatman dataset, FIG. 10 results of the Ŝ-optimization, (a) & (b) original dose/effect curves, (c) & (d) Ŝ-optimized curves, Akt3 assay, Whatman dataset, FIG. 11 control well values after Z' optimization, Akt3 assay, PV dataset, FIG. 12 the development of the Z'-value, Akt3 assay, PV dataset, FIG. 13 a table indicating the Ŝ-optimized parameters, Akt3 assay, PV dataset, FIG. 14 the development of the Ŝ-value, Akt3 assay, PV dataset, FIG. 15 results of the Ŝ-optimization, (a) & (b) original dose/effect curves, (c) & (d) Ŝ-optimized curves, Akt3 assay, PV dataset, FIG. 16 Ŝ-value with Z'-optimization of the Akt3 assay, Whatman dataset on the left, PV-dataset on the right, FIG. 17 Z'-value with Ŝ-optimization of the Akt3 assay, Whatman dataset on the left, PV-dataset on the right, FIG. 18 Ŝ-optimization of the U2OS-cells of the $ET_4R$ assays, dataset 070116_Plate 1, non-optimized dose/effect curve on the left, optimized dose/effect curve on the right, FIG. 19 Dose/effect-curve after Ŝ-optimization with penalty term of the U2OS-cells, dataset 070116_Plate1, FIG. 20 Ŝ-optimized parameters with penalty term of the U2OS-cells, dataset 070116_Plate1, FIG. 21 a table of the Ŝ- and Z'-values during the Ŝ-optimization with penalty term of the U2OS-cells, dataset 070116_Plate1, FIG. 22 the application of the parameters optimized with regard to the dataset 070116_Plate1, to the U2OS data of the $ET_4R$ assay, FIG. 23 the application of the parameters optimized with regard to the dataset 070116_Plate1, to the other U2OS data of the $ET_4R$ assay, FIG. 24 a table of the Ŝ-optimized parameters with penal term of the CHO-cells, dataset Afo_080129_CHO_ETAR, and FIG. 25 dose/effect curves after Ŝ-optimization with penal term of the CHO-cells.

The basic idea of a parameter optimization for high-content analysis in high-throughput screening, as provided in accordance with the disclosure, resides in that, with the aid of the results of the statistical evaluation, the settable control parameters will be iteratively improved by way of reference, possibly without prior setting of the parameters on the basis of biological substantiation (FIG. 1).

Hereunder, it will be explained what is to be understood under an "optimal setting", and suitable statistical objective functions will be defined.

As already described, the method starts with a plurality of samples which preferably are provided in individual sample chambers ("wells") of a multi-well sample carrier. The basis of the following statistical analyses is, in each case, an activity value, hereunder also referred to as a "well measure", which will be determined by measuring a sample including a known test substance concentration by use of the evaluation rule.

Z'-Value

The Z'-value is a statistical characteristic which makes a statement on the quality of the assay. This value is based on well measures which were detected on reference samples with test substances of a known level of activity ("positive control") and, respectively, without a test substance ("negative control").

$$Z' := 1 - 3 \frac{\sigma_{pos} + \sigma_{neg}}{|\mu_{pos} - \mu_{neg}|},$$

wherein $\mu_{pos}, \mu_{neg}$ and $\sigma_{pos}, \sigma_{neg}$ are the average values and the standard deviations of the well measures of the positive and respectively negative control wells. For Z', obviously, Z'≤1 holds true. The quality of the analysis will be the better, the closer Z' comes to 1, and thus Z' is a suitable objective function. There will occur the optimization problem $$\min_{x \in \mathbb{R}^n} f(x) \text{ wherein } (x) := -Z'(x) \quad (2.1)$$

with n steady parameters $x \in E^n$. The expenditure of an evaluation of f=−Z' is relatively high because, for instance, in the Akt3 assay, it is required to evaluate as many as 16 control wells, i.e. 96 images.

Dose/Effect Curve

The dose/effect curve is a customarily used instrument for analysis of an assay with different doses. This curve represents the interrelation between the substance activity and the dose of the active agent. Often, the complete interrelation between dose and effect can be represented only by visually spreading out several orders of magnitude of the dose; thus, these will usually be represented logarithmically.

Depending on which active agent is used and which measure is used for describing the effect, the dose/effect curve can take nearly any shape while, nonetheless, most curves correspond to a standard form. This standard dose/effect curve is referred to as a Hill equation and is a logistic function depending on four parameters. It is defined as $$r(d) := \begin{cases} r_0 + \dfrac{r_{max} - r_0}{1 + \left(\dfrac{EC_{50}}{d}\right)^s} = r_0 + \dfrac{r_{max} - r_0}{1 + 10^{s(\log_{10} EC_{50} - \log_{10}(d))}}, & \text{für } d > 0, \\ r_0, & \text{für } d = 0, \end{cases}$$

(Hill Equation)

wherein $r_0$ designates the state without stimulation and $r_{max}$ designates the maximum effect. The parameter s influences the slope (Hill slope) of the curve, and $EC_{50}$ is the dose which will result in "half the effect" $r_0 + r_{max}/2$. The description given hereunder will be restricted to this dose/effect model. The four parameters $r_0$, $r_{max}$, s and $EC_{50}$ can be determined by the least squares method with the aid of nonlinear regression:

Let it be assumed that $m_1, \ldots, m_n$ are the measured well measurements with appertaining doses $d_1, \ldots, d_n$. To guarantee reproducibility, the same doses will often be tested a plurality of times so that the $d_i$ values do not necessarily have to be different within each pair. For determining the compensating curve r(d), there will then be solved the minimizing problem $$S := \frac{1}{n}\sum_{i=1}^{n}(m_i - r(d_i))^2 \to \min_{r_0, r_{max}, s, EC_{50}}.$$

The residuum S represents the mean square deviation from the model curve.

For solving this non-linear regression, the above equation will be iteratively solved with suitable starting values for $r_0$, $r_{max}$, s und $EC_{50}$. The selection of these values can influence the convergence of the solving method, and, in the worst case, a wrong selection can even cause a divergence of the method.

For the Hill equation, it is possible to reach starting parameters by interpretation of the parameters $r_0$, $r_{max}$, s and $EC_{50}$. As starting values for the minimal and the maximal effect $r_0$ und $r_{max}$, there will be selected:

$$r_0 = \min_{i=1,\ldots,n}(m_i) - \varepsilon\, bzw.$$

$$r_{max} = \max_{i=1,\ldots,n}(m_i) + \varepsilon$$

with a very small $\varepsilon > 0$. From this, there follows, for $d>0$, $r_0 < r < r_{max}$:

$$r = r_0 + \frac{r_{max} - r_0}{1 + 10^{s(\log_{10} EC_{50} - \log_{10}(d))}}$$

$$= \frac{r_0 \cdot 10^{s(\log_{10} EC_{50} - \log_{10}(d))} + r_{max}}{1 + 10^{s(\log_{10} EC_{50} - \log_{10}(d))}} \Leftrightarrow r - r_{max}$$

$$= (r_0 - r)10^{s(\log_{10} EC_{50} - \log_{10}(d))} \Leftrightarrow \underbrace{\log_{10}\left(\frac{r - r_{max}}{r_0 - r}\right)}_{=:\tilde{r}}$$

$$= s(\log_{10} EC_{50} - \log_{10}(d))$$

and thus, d will develop linearly with regard to $\log_{10}(d)$. Because of the definitions, $$\frac{m_i - r_{max}}{r_0 - m_i} > 0,$$

i=1, ..., n, holds true and thus $$\tilde{m}_i := \log_{10}\left(\frac{m_i - r_{max}}{r_0 - m_i}\right)$$

is defined for i=1, ..., n.

The linear regression $$\sum_{i=1}^{n}(\tilde{m}_i - \tilde{r}(d_i))^2 =$$

$$\sum_{i=1}^{n}\left(\log_{10}\left(\frac{m_i - r_{max}}{r_0 - m_i}\right) - s(\log_{10} EC_{50} - \log_{10}(d))\right)^2 \to \min_{s, EC_{50}}$$

will yield starting values $$s = -\frac{\sum_{i=1}^{n}(\log_{10}(d_i) - \mu_{\log_{10}(d)})(\tilde{m}_i - \mu_{\tilde{m}})}{\sum_{i=1}^{n}(\log_{10}(d_i) - \mu_{\log_{10}(d)})^2},$$

$$\log_{10} EC_{50} = \frac{\mu_{\tilde{m}} + s\mu_{\log_{10}(d)}}{s},$$

with the average values $$\mu_{\log_{10}(d)} := \frac{1}{n}\sum_{i=1}^{n}\log_{10}(d_i)$$

and $$\mu_{\tilde{m}} := \frac{1}{n}\sum_{i=1}^{n}\tilde{m}_i.$$

Ŝ-Value

According to the disclosure, also the residuum of the dose/effect regression can be used for optimization. For n measured well measures $m_i$(i=1 ... n) with appertaining doses $d_i$(i=1 ... n) kurz $$d_i(i=1\ldots n)\, kurz\, (d_i, m_i)_{i=1}^{n},$$

non-linear regression of the dose/effect curve will result in $$r: \mathbb{R} \to \mathbb{R},$$

$$d \mapsto r_0 + \frac{r_{max} - r_0}{1 + \left(\frac{EC_{50}}{d}\right)^s}.$$

A small residuum $$\hat{S} := \frac{1}{n}\sum_{i=1}^{n}(m_i - r(d_i))^2$$

is an indicator of a good adaptation to the Hill equation model. The residuum Ŝ, however, is very decisively dependent on the range of the curve $|r_{max} - r_0|$. Therefore, it is preferred that, after regression, a normalization of the dose/effect curve and of the well measures is performed:

$$\hat{r}(d) := \frac{r(d) - r_0}{|r_{max} - r_0|},$$

$$\hat{m}_i := \frac{m_i - r_0}{|r_{max} - r_0|},$$

$$i = 1,\ldots,n.$$

The amount $$\frac{\hat{r}(d)}{100}$$

now indicates the percentage of the excitation of an average cell by the dose d. The residuum $\hat{S}$ belonging to $\hat{r}$ will behave as follows:

$$\hat{S} := \frac{1}{n}\sum_{i=1}^{n}(\hat{m}_i - \hat{r}(d_i))^2$$

$$= \frac{1}{n}\sum_{i=1}^{n}\left(\frac{m_i - r_0}{|r_{max} - r_0|} - \frac{r(d_i) - r_0}{|r_{max} - r_0|}\right)^2$$

$$= \frac{1}{(r_{max} - r_0)^2}\frac{1}{n}\sum_{i=1}^{n}(m_i - r(d_i))^2$$

$$= \frac{1}{(r_{max} - r_0)^2}S.$$

Figure 2:
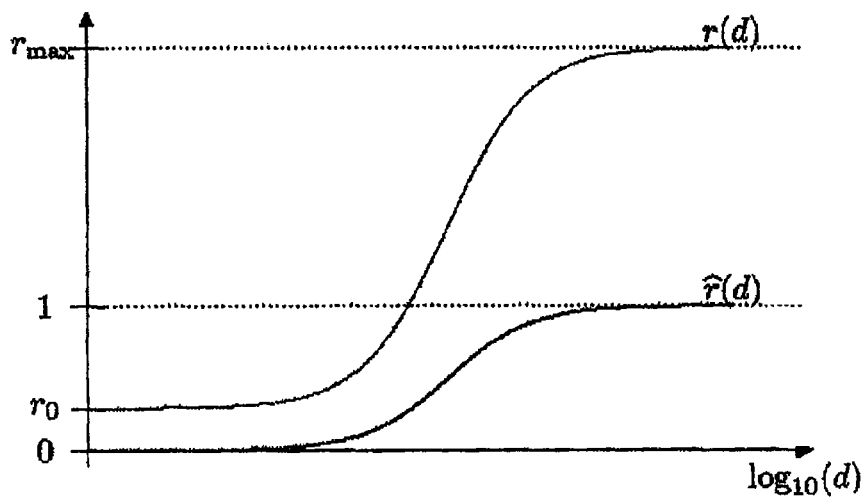

Also the now derived residuum of the normalized dose/effect curve $$\hat{S} = \frac{1}{(r_{max} - r_0)^2}S$$

is suited for optimization because, due to the normalization (see FIG. 2), it is independent from the range $|r_{max} - r_0|$ and a small residuum is to say that a good adaptation to the Hill equation model exists. The value $|r_{max} - r_0|$ in this context is also referred to as the dynamic range. Thus, a further reasonable optimization problem is $$\min_{x \in \mathbb{R}^n} f(x) \text{ wherein } {}^x(x) := \hat{S}(x), \quad (2.2)$$

with n steady parameters $x \in \mathbb{R}^n$. It should be considered that this optimization is much more complex than equation (2.1) because, for a functional evaluation of $f = \hat{S}$, one will have to analyse not only the control wells but all wells.

Relationship Between Z'- and Ŝ-Values:

For computing the Z'-value, use is made only of the control wells, i.e. signals with minimal and maximal amplitudes. In the Ŝ-value, by contrast, there are included, apart from the signals without addition of an active substance and with maximum dose, also images of cells that are only partially excited. Thus, when performing the optimization with regard to the Z'-value according to equation (2.1), it may happen that, although the standard deviations in the control wells become very small, strong deviations will occur in case of deviations in the medium range, i.e. the residuum of the dose/effect regression will be enlarged. Or, expressed in a different manner: The case may occur that the Ŝ-value will considerably deteriorate during the Z'-value optimization.

If, however, one minimizes Ŝ according to equation (2.2), the optimization will include signals of minimum and maximum effect as well as finer gradations therebetween. As a result, one does not have to expect a significant degradation of the Z'-value during the Ŝ-optimization.

Next, it will have to be considered which parameters are useful for optimization. In the automatic setting of segmentation parameters, the optimization of the objective function value should not be performed at the expense of a good object detection. An impeccable detection of the objects is the basic precondition for the cell analysis.

Further, it is preferred that no optimization is performed via exclusion parameters. These parameters shall exclude those cells from analysis which have not been optimally scanned or are not alive anymore. The segregation of these pathological cases can be performed e.g. with the aid of limit values of the magnitudes and the intensities. Also an optimization via these parameters is not desired because the pathological cells should not influence the analysis. Preferably, the exclusion parameters are determined on the basis of biological considerations.

Thus, for optimization, there still remain all parameters which are included in the model describing the activity of the cell.

In selecting the optimization routine, it is preferred, according to the disclosure, to give consideration to the following:

i) It may happen that the object functions $-Z'$ or $-\hat{S}$ which are to be minimized cannot be differentiated with regard to x.

ii) A function evaluation is normally very expensive. For an evaluation of Z', the control wells have to be analysed, and for an evaluation of Ŝ, it is even required to analyse all wells.

The first property of f implies that a derivation-free method has to be used. Also an approximation of the gradient with the aid of finite differences may happen to be not satisfactory if f has numerous local minima. The second restriction in the selection of an optimization method can be ameliorated a bit because the images can be analysed independently from each other, thus rendering it possible to subdivide the data (into wells or even subwells). Accordingly, f could be easily evaluated on a plurality of computers in parallel. As second amelioration consists in that the segmentation has to be carried out only once because no optimization via segmentation parameters is intended. The segmentation results can be stored and always be used again.

Due to item i), optimization is performed with the aid of the method by Nelder and Mead. This robust, derivation-free method for optimization of non-linear functions is of excellent use for the present optimization problems. It be noted herein that this work does not deal with finding the best possible optimization routine. Instead, it is intended to derive a reasonable object function for automatic improvement of the quality of high-throughput screening and to demonstrate the practicability of the parameter optimization according to FIG. 1 by way of exemplary assays.

The Nelder-Mead method is a heuristically motivated, derivation-free minimizing method. As its basic structure, it uses a simplex of approximations of an optimal solution and performs an iterative transition to a simplex with improved object function values. The description is oriented on Alt, W.: Nichtlineare Optimierung. Vieweg 2002, and Kelley, C. T.: Iterative Methods for Optimization. Society for Industrial & Applied Mathematics, 1999.

Hereunder, now, the optimization tasks according to equations (2.1) and (2.2) shall be applied to the exemplary assays. The calculations were performed on a notebook including a Pentium M processor with 1.8 GHz, and the indicated computational times will always refer to this system.

Example I

Akt3 Assay

The first example of the parameter optimization is the Akt3 assay wherein, first, the Whatman dataset is processed, whose data were used for developing the HCS analysis. Later, the parameters were set with the aid of the optimization problems according to equations (2.1) and (2.2) in a manner allowing the model to furnish good results also for the PV dataset.

Whatman Dataset:

The model was developed for the Whatman dataset and in this application is able to yield very good results. Then, it was examined whether it was possible to achieve a still better adjustment of the parameters defined at exemplary cells.

Z'-Maximization:

The Z'-value of the Whatman dataset of the Akt3 assay resulted as Z'=0.6347. The measure used for the description of the activity $$\text{cell measure}:=Q_{q1}(\text{cytoplasm mask})-Q_{q2}(\text{membrane mask})$$

depends on six parameters. These are the two amounts of the quantiles ($q_1=0.8$ and $q_2=0.9$), the two limits of membrane mask (0 und 4) and the two limits of the cytoplasm mask (7 und 13).

Figure 3:
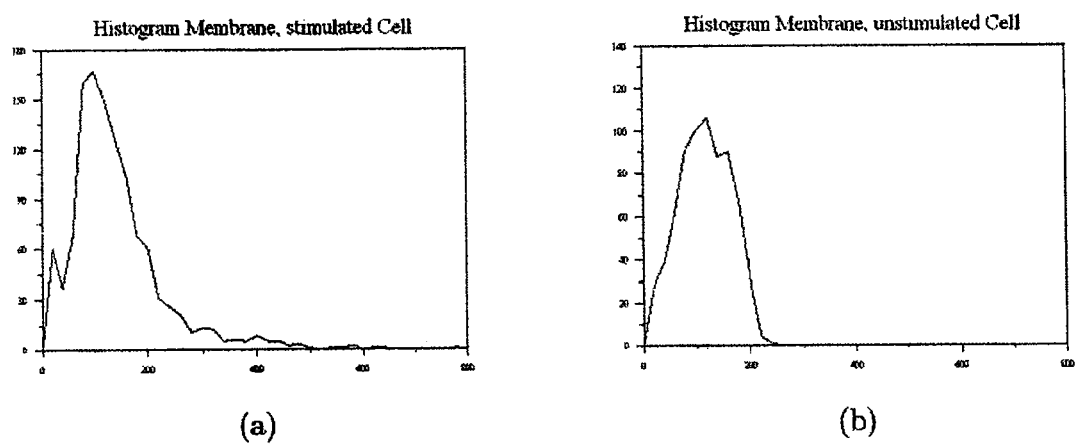
Figure 4:
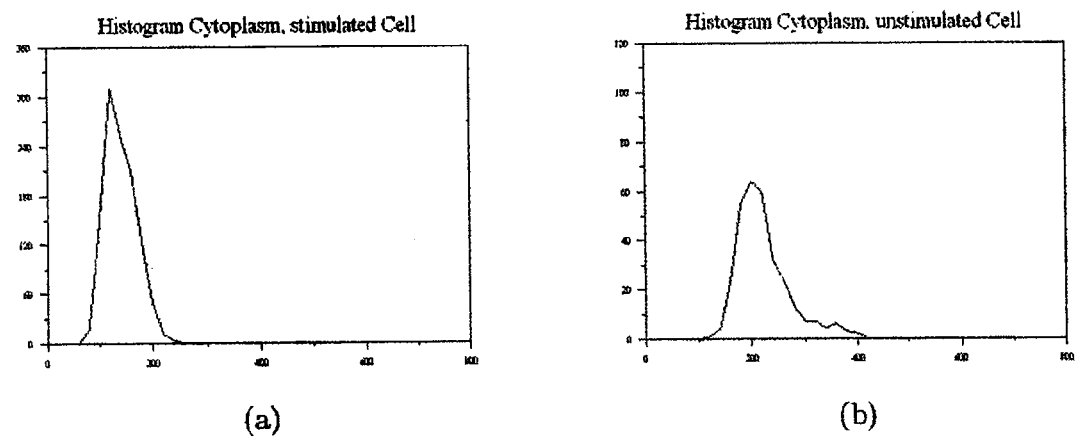
Figure 5:
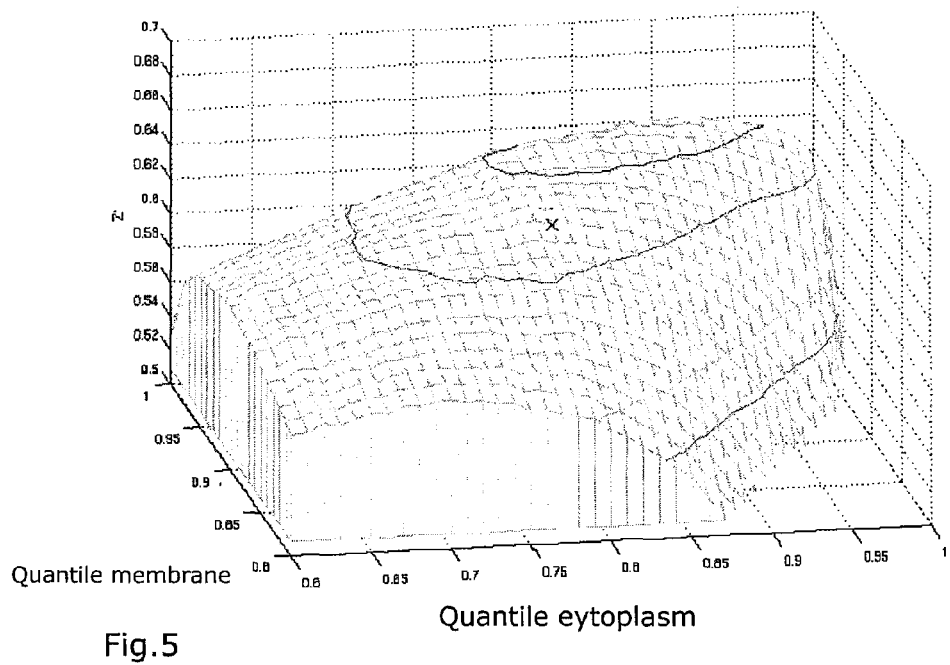

First, an optimization of the two quantiles is performed. The algorithm starts at $(q_1, q_2)^T=(0.8, 0.9)^T$ and after 64 function evaluations will lead to a value $$Z'=0.6552$$

with the quantiles $(q_1, q_2)^T=(0.8463, 0.9654)^T$. Since the optimization is not performed via the segmentation parameters, the segmentation was performed only once, and the results were stored. This reduces the expenditure of a function evaluation of f=Z' from five minutes to about 30 seconds. Thus, about 32 minutes passed during the optimization of the two quantiles. Apparently, the quantiles estimated on the basis of the exemplary histograms (FIGS. 3 and 4) were not optimal. FIG. 5 shows the relation between the quantiles and the Z'-value, the cross marking the initial parameters $(q_1, q_2)^T=(0.8, 0.9)^T$. In optimizing the parameters, it is to be kept in mind that the allowable range of the parameters is $$[0, 1]^2 \subsetneq R^2.$$

The problem is solved by projection onto $[0, 1]^2$, i.e. it is defined for $x \notin [0, 1]^2$ (see FIG. 5):

$$Z'(x) := Z'(y^*),$$

wherein $$\|x - y^*\| = \inf_{y \in [0,1]^2} \|x - y\|.$$

Next, all six parameters might be optimized analogously. Instead, the model will first be slightly modified so as to obtain further parameters. For describing the activity of a cell, there is defined the $$\text{cell measure}:=\lambda \cdot (Q_{q1}(\text{cytoplasm mask}))^{\mu_1} - (Q_{q2}(\text{membrane mask}))^{\mu_2}$$

with a factor $\lambda$ and the powers $\mu_1$ and $\mu_2$. The model depends on nine variables and is a generalization of equation (1.1). First, the factor $\lambda=1$ and the powers $\mu_1$ and $\mu_2=1$ will be set.

The next step is to be the optimization of this new model with regard to the nine parameters. For the object functions (2.1) and (2.2), it has been proven advantageous to optimize the parameters in a step-wise manner because the result of the Nelder-Mead algorithm is delicately dependent on the starting parameters. Next, for this reason, it is exclusively the powers µ1 and µ2 that will be optimized, and the rest of the parameters will be retained. After 51 function evaluations and a scarce 26 minutes, the optimization resulted in $$Z'=0.7227,$$

with powers $(\mu_1, \mu_2)^T=(0.5223, 0.5093)^T$.

The last step is the optimization of all nine parameters. As starting values, the already preselected quantiles $(q_1, q_2)^T=(0.8463, 0.9654)^T$ and powers $(\mu_1, \mu_2)^T=(0.5223, 0.5093)^T$ will be selected.

The limits of the membrane and cytoplasm mask start at $(0, 4)^T$ and respectively $(7,13)^T$, and the factor $\lambda$ starts at 1. Thus, the result of further 207 function evaluations will be $$Z'=0.8096.$$

By the optimization, the control parameters have changed as follows:

| | | |
|---|---|---|
| $q_1$ = 0.8 → 0.5911 | Zone 1: | 0 → 2.0723 |
| $q_2$ = 0.9 → 1.0 | | 4 → 4.6498 |
| $\mu_1$ = 1.0 → 0.5183 | Zone 2: | 7 → 7.161 |
| $\mu_2$ = 1.0 → 0.5108 | | 13 → 11.5971 |
| $\lambda$ = 1.0 → 1.3341 | | |

Figure 6:
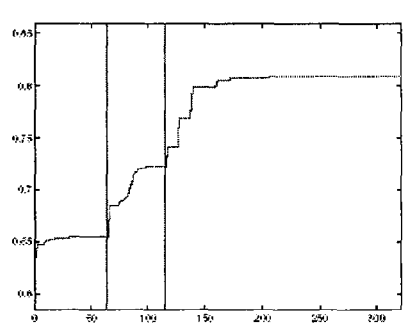
Figure 7:
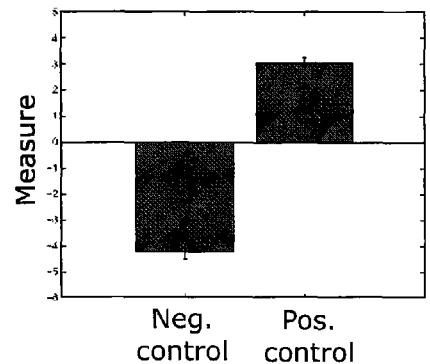

On the whole, the three-stage optimization with 322 function evaluations took about 2.5 hours, and the Z'-value was very distinctly improved. FIG. 6 once again shows the evaluation of the control wells of the optimized measure, and FIG. 7 represents the development of the Z'-value in dependence on the function evaluations. The red markings designate the three stages.

Ŝ-Minimization:

After the Z'-value has been significantly improved, an analog course will be taken for the Ŝ-value. The subsequent table indicates in which doses the employed substances were used.

| | 1 | 2 | 3 | 4 | 5 | 6 | 7 | 8 | 9 | 10 | 11 | 12 |
|---|---|---|---|---|---|---|---|---|---|---|---|---|
| A | Neg. Ctrl. | 0.0 | 2.0 | 3.9 | 7.8 | 15.6 | 31.3 | 62.5 | 125 | 250 | 500 | Pos. Ctrl. |
| B | Neg. Ctrl. | 0.0 | 2.0 | 3.9 | 7.8 | 15.6 | 31.3 | 62.5 | 125 | 250 | 500 | Pos. Ctrl. |

-continued

| | 1 | 2 | 3 | 4 | 5 | 6 | 7 | 8 | 9 | 10 | 11 | 12 |
|---|---|---|---|---|---|---|---|---|---|---|---|---|
| C | Neg. Ctrl. | 0.0 | 2.0 | 3.9 | 7.8 | 15.6 | 31.3 | 62.5 | 125 | 250 | 500 | Pos. Ctrl. |
| D | Neg. Ctrl. | 0.0 | 2.0 | 3.9 | 7.8 | 15.6 | 31.3 | 62.5 | 125 | 250 | 500 | Pos. Ctrl. |
| E | Neg. Ctrl. | 0.0 | 0.3 | 0.6 | 1.3 | 2.5 | 5 | 10 | 20 | 40 | 80 | Neg. Ctrl. |
| F | Neg. Ctrl. | 0.0 | 0.3 | 0.6 | 1.3 | 2.5 | 5 | 10 | 20 | 40 | 80 | Neg. Ctrl. |
| G | Neg. Ctrl. | 0.0 | 0.3 | 0.6 | 1.3 | 2.5 | 5 | 10 | 20 | 40 | 80 | Neg. Ctrl. |
| H | Neg. Ctrl. | 0.0 | 0.3 | 0.6 | 1.3 | 2.5 | 5 | 10 | 20 | 40 | 80 | Neg. Ctrl. |

Neg. Control = 0.25% DMSO,
Pos. Control = 300 nM Wortmannin
Wortmannin (nM)
LY294002 (µM) 0.25% DMSO For the dose/effect analysis, only columns 2 to 11 of the microtitration plate are used, as mentioned above. Columns 1 and 12 are not used because, in the minimization of the Ŝ-value, all doses have to be weighted equally and because only the antagonist Wortmannin was used for the positive control signals. Thus, 12 data items exist per dose and active substance, and for computing the dose/effect curves, 40 well measures have to be examined per active substance.

Optimization was again performed in three stages; here, however, only the results after the third step are shown. The expenditure of an evaluation of f=Ŝ is about four minutes, wherein the segmentation again will be performed once and the segmentation results will be stored for reuse. In this optimization, which is much more complex than the Z'-maximization, only this method makes it possible to perform the process within an acceptable time.

The Ŝ-value of the Whatman dataset of the Akt3 assay prior to optimization will be obtained as $\hat{S}=1.01 \cdot 10^{-2}$ while composed as the sum of the individual residues $\hat{S}_{Wortmannin}$ and $\hat{S}_{LY294002}$ of the substances Wortmannin and LY294002. The individual residues are obtained from $\hat{S}_{Wortmannin}=7.28 \cdot 10^{-3}, \hat{S}_{LY2940002}=2.79 \cdot 10^{-3}$.

The minimization of Ŝ after 314 function evaluations and about 21 hours had the result $\hat{S}=4.15 \cdot 10^{-3}$ wherein $\hat{S}_{Wortmannin}=3.29 \cdot 10^{-3}, \hat{S}_{LY294002}=8.58 \cdot 10^{-4}$.

The change of the parameters by the Ŝ-optimization is shown in the table of FIG. 8. FIG. 9 shows the temporal development of Ŝ during optimization, and FIG. 10 graphically represents the final result as a dose/effect curve. In the first row, the original dose/effect curves are shown again, and the optimized curves are shown in the second row. After optimization, the well measures are significantly better adapted to the Hill equation model.

PV Dataset:

In contrast to the Whatman dataset, the quality of the PV dataset with Z'=0.3314 is not satisfactory. Since the model according to equation (1.1) was derived for analysis of the Akt3 assay for the Whatman dataset and since the datasets strongly differ from each other in contrast and brightness, the bad Z'-value of course does not come as a surprise. Next, it was tried to automatically adapt the parameter settings in such a manner that the model would be useful also for analysis of the PV dataset. The parameter optimization used for the Whatman dataset was analogously applied to the PV dataset, and the results are shown in FIG. 10.

Z'-Maximization:

The three-stage optimization of the Z'-value after 674 function evaluations and slightly more than 5.5 hours resulted in

Z'=0.7878.

By the optimization, the parameters changed as indicated hereunder:

| | | |
|---|---|---|
| $q_1 = 0.8 \rightarrow 0.0$ | Zone 1: | $0 \rightarrow -0.9840$ |
| $q_2 = 0.9 \rightarrow 1.0$ | | $4 \rightarrow 1.4675$ |
| $\mu_1 = 1.0 \rightarrow 0.2129$ | Zone 2: | $7 \rightarrow 7.0288$ |
| $\mu_2 = 1.0 \rightarrow 0.1398$ | | $13 \rightarrow 14.3346$ |
| $\lambda = 1.0 \rightarrow 1.2203$ | | |

FIG. 11 shows the evaluation of the control wells of the optimized model, and FIG. 12 shows the development of the Z'-value in dependence on the function evaluations. The markings again indicate the three stages.

Figure 15:
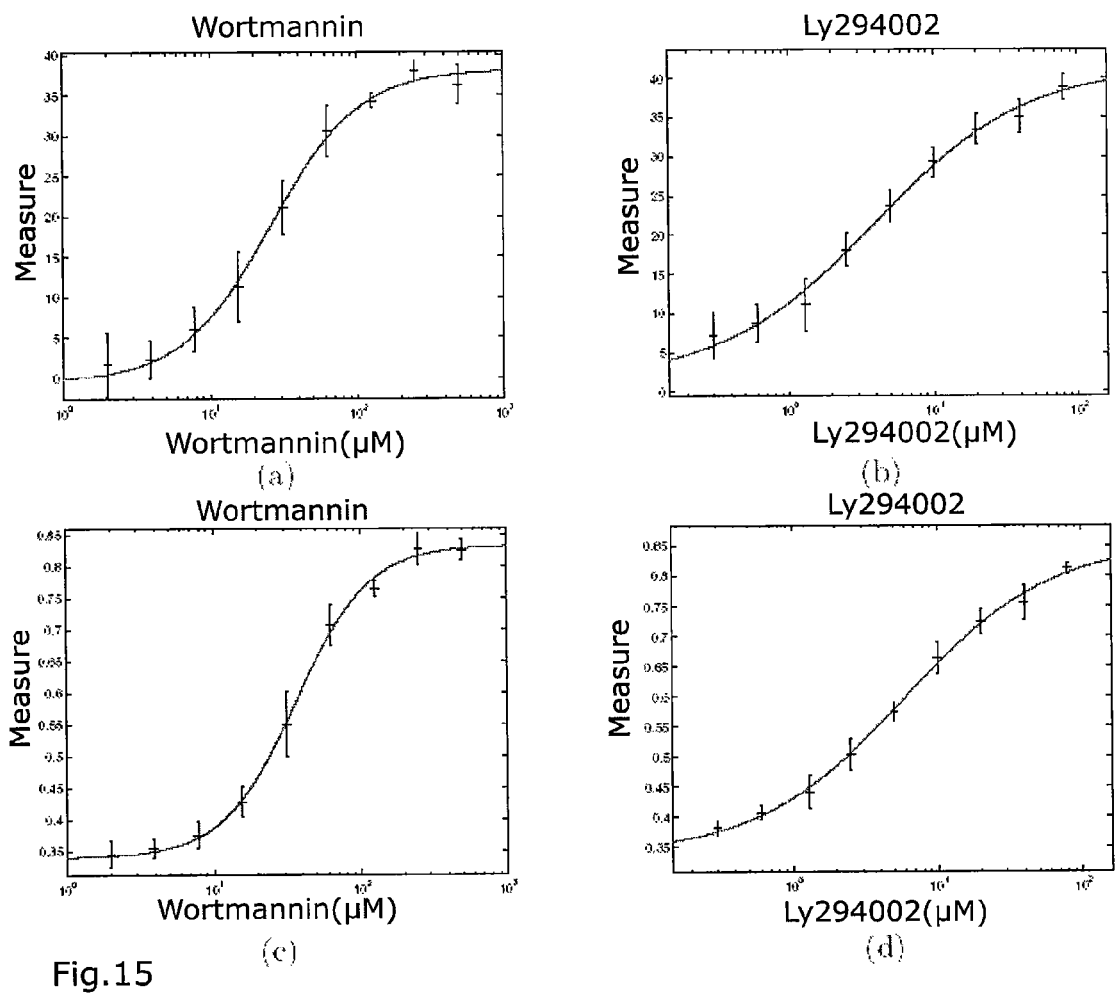

Ŝ-Minimization:

The Ŝ-value of the PV-dataset of the Akt3 assay prior to optimization will be obtained as $\hat{S}=7.70 \cdot 10^{-3}$ while being the sum of the individual residues $\hat{S}_{Wortmannin}=4.60 \cdot 10^{-3}$ and $\hat{S}_{LY294002}=3.10 \cdot 10^{-3}$ of the substances Wortmannin and LY294002. The minimization of Ŝ after 235 function evaluations and about 15.5 hours resulted in $\hat{S}=3.67 \cdot 10^{-3}$ $\hat{S}_{Wortmannin}=2.34 \cdot 10^{-3}, \hat{S}_{LY294002}=1.33 \cdot 10^{-3}$ with $\hat{S}_{Wortmannin}=2.34 \cdot 10^{-3}, \hat{S}_{LY294002}=1.33 \cdot 10^{-3}$ The change of the parameters by the Ŝ-optimization is shown in the table of FIG. 13. FIG. 14 shows the temporal development of Ŝ during optimization, and FIG. 15 graphically represents the final result as a dose/effect curve.

Figure 16:
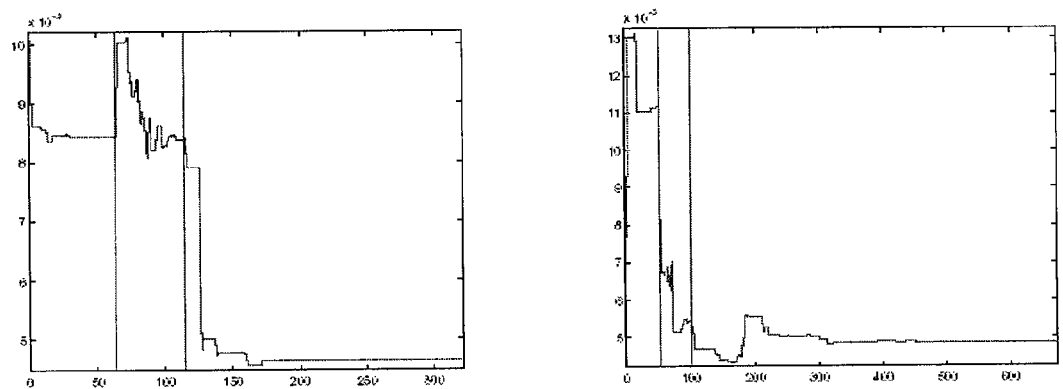

FIG. 16 shows the temporal development of the Ŝ-value upon Z'-optimization. While, as expected, the Z'-value will increase monotonously (cf. FIG. 6 or FIG. 12), the Ŝ-value will partially change in a very disadvantageous manner. In analogy thereto, FIG. 17 shows the Z'-value upon Ŝ-minimization. Also here, one can partially detect developments for the worse that the non-optimized value has taken, although by far not as massively as in Z'-optimization.

Example II

ET$_A$R Assay

The Acapella default parameters of the spot detection module, when used for the ET$_A$R assay, yielded bad results. Instead of setting these manually on the basis of empirical data and biological argumentation, use is made of a parameter optimization with the aid of the Ŝ-value according to equation (2.2). Thus, the parameter optimization of the ET$_A$R assay is a much bigger challenge than that of the Akt3 assay, first because one has to begin with a very bad starting value and, second, because one should not use information on the functionality of the module.

U2OS-Cells:

The Ŝ-minimization will first be applied to the dataset 070116_Plate1 of the U2OS-cell. The model depends on seven parameters: Five parameters will influence the spot detection module, and two further parameters will be obtained by definition of the search range for spots. This is defined as (−5, 5). The optimization shall again be carried out in several stages. First, the five parameters of the spot detection module will be preset. Then, in a second step, all parameters will be included in the optimization.

The Ŝ-value prior to optimization will be $$\hat{S} = 0.2470.$$

The minimization after 264 function evaluations and about 15.5 hours (i.e. about 3.5 minutes per evaluation) had the result $$\hat{S} = 0.0480.$$

In FIG. 18, the non-optimized dose/effect curve is shown on the left side, and the optimized curve is shown on the right-hand side.

Although indeed the Ŝ-value has considerably improved, which is also evident from the error bar in FIG. 18, the result is not as expected. According to the description of the assay, it would have to be anticipated that, for lower doses, nearly no cells should have a spot and, for very high doses, nearly each cell should have at least one spot. A possible reason for this strange result is that the residuum will be small also if, in the spot detection module, the threshold values are set to such extreme values that all measures after 0% or 100% will be printed. If the measures are near these limits, all too large mutual deviations can obviously not occur anymore. Apparently, one has entered a local minimum which significantly deviates from the searched-for parameter setting.

In order to prevent this phenomenon, use was made of the prior knowledge that non-stimulated cells have no intracellular fluorescence, whereas nearly all stimulated cells do have such fluorescence. This knowledge will be integrated as a penalty term into the optimization, and the value adapted to the ET$_A$R assay will be defined:

$$\hat{S}_{ET_AR} := \hat{S} - \lambda (r_{max} - r_0)^2 \quad (2.3)$$

with a constant $\lambda > 0$. The new object function will reward large ranges $|r_{max} - r_0|$ and punish small ones. Now, $\lambda > 0$ will be selected in such a manner that $$\hat{S} \approx \lambda (r_{max} - r_0)^2.$$

The minimizing of the object function (2.3) with $\lambda = 0.001$ after 445 function evaluations and 26 hours had the result $$\hat{S} = 7.13 \cdot 10^{-3} \text{ and } Z' = 0.6343$$

FIG. 19 shows the dose/effect curve as optimized with respect to equation (2.3), and the table in FIG. 20 indicates the change of the seven parameters during optimization. In FIG. 21, the development of Ŝ and respectively Z' during optimization is plotted. It is to be noted here that Ŝ does not drop monotonously, since an optimization was performed with regard to $\hat{S}_{ET_AR}$.

Instead of now analogously optimizing also the other U2OS-datasets, the optimal parameters for the first microtitration plate from the table (FIG. 20) were applied to the remaining three datasets. Since the scans have been made under comparable conditions, the parameters should yield similarly good dose/effect curves. There will be obtained the values listed in FIG. 22.

|  | Z' | Ŝ | $r_o$ | $r_{max}$ | $\log_{10} EC_{50}$ | s |
|---|---|---|---|---|---|---|
| 070116_Plate1 | 0.6343 | 7.13 · 10$^{-3}$ | 8.5661 | 70.4336 | 0.9436 | 3.3240 |
| 070116_Plate2 | 0.6825 | 6.16 · 10$^{-3}$ | 9.3827 | 71.4504 | 1.1505 | 3.1752 |
| 060622_ETAR_Draq | 0.8233 | 2.40 · 10$^{-3}$ | 3.8020 | 80.0043 | 1.1768 | 3.1063 |
| AFo_U2OS_20xW_070209 | 0.8521 | 4.31 · 10$^{-3}$ | 4.9235 | 68.2637 | 0.9190 | 3.3525 |

FIG. 23 shows the three curves individually with error bars and additionally, for better understanding, all of them together in one plot.

CHO-Cells:

Finally, the Ŝ-optimization with penalty term was applied, in accordance to equation (2.3), to the CHO cell. As in case of the U2OS-cells, optimization is performed in the two stages. The dataset Afo_070129_CHO_ETAR was optimized and the parameters were then applied to the second dataset. Since the data of the U2OS- and the CHO-cells bear a resemblance to each other, the results of the table shown in FIG. 20 were chosen as starting parameters. These will yield the comparatively good results.

|  | Z' | Ŝ |
|---|---|---|
| AFo_070129_CHO_ETAR | −0.1793 | 30.77 · 10$^{-3}$ |
| AFo_CHO_ETAR_20x_070221 | −0.1958 | 28.07 · 10$^{-3}$ |

The CHO-datasets, with ten subwells per well, are larger than the U2OS-cells, and the evaluation, taking 10 minutes, is distinctly more complex. After a total of 330 function evaluations and 55 hours, the optimization with the target function (2.3) and $\lambda = 0.001$ had the following results:

|  | Z' | Ŝ |
| --- | --- | --- |
| AFo_070129_CHO_ETAR | 0.3041 | $12.41 \cdot 10^{-3}$ |
| AFo_CHO_ETAR_20x_070221 | 0.3025 | $13.08 \cdot 10^{-3}$ |

|  | $r_0$ | $r_{max}$ | $\text{Log}_{10}\text{EC}_{50}$ | s |
| --- | --- | --- | --- | --- |
| AFo_070129_CHO_ETAR | 24.3209 | 65.0752 | 1.2327 | 4.9058 |
| AFo_CHO_ETAR_20x_070221 | 19.3795 | 69.2861 | 1.1153 | 11.0819 |

Figures 24, 25:
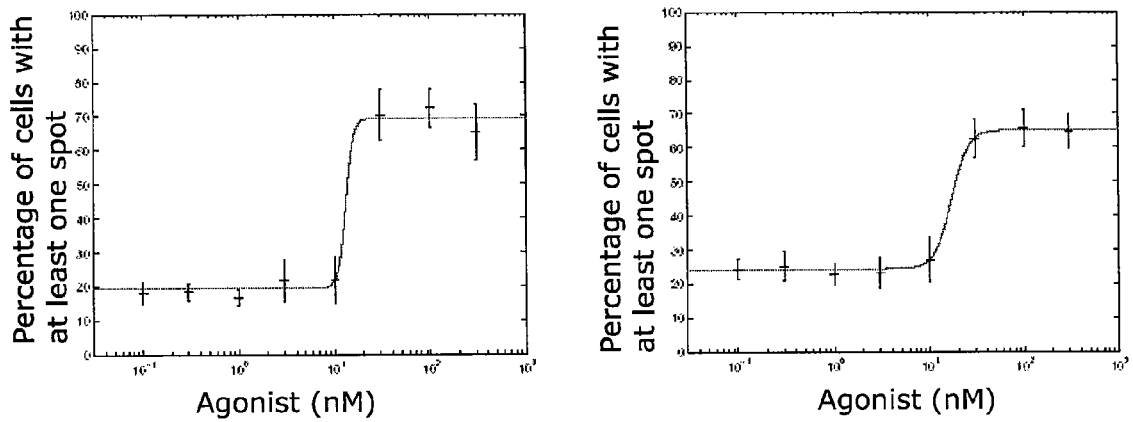

It should be noted that, here, the dataset AFo_070129_CHO_ETAR was optimized and the result parameters were applied to the second dataset. In the table presented in FIG. 24, the seven optimized parameters are indicated, and FIG. 25 shows the corresponding dose/effect curves. The developments of the Ŝ- and the Z'-value are similar to those the above U2OS-cells and thus will not be shown once more.

CONCLUSION AND NOTES ON THE EXAMPLES

The application of the Nelder-Mead parameter optimization with regard to the Z'-value onto the Akt3 assay has achieved a considerable improvement. Particularly the optimization of the PV dataset yielded astonishing results, and it is only due to these optimized parameters that the high-content analysis can be used here at all. Nonetheless, a decisive disadvantage became evident in the optimization with respect to Z': Since only the control wells will be included in the computation of the Z'-value, the residuum of the dose/effect regression may deteriorate during optimization.

Also the application of the parameter optimization with regard to the S'-value onto the Akt3 data improved the parameter setting, and the residuum of the dose/effect regression was reduced. During this optimization, also the Z'-value increased considerably because the computation of is performed also under inclusion of minimal and maximal doses.

Still more impressive than the parameter optimization is the application for the $ET_4R$ assay. By the introduction of the penalty term, it was made possible to adapt the minimizing function to the properties of the assay. Particularly in the U2OS-cells, the optimizing routine resulted in a very considerable improvement although very bad starting parameters were selected and no information existed about the functionality of the spot detection module. Another very positive aspect resides in that the results of the optimization with respect to a dataset were applicable also to the other datasets which had been recorded under similar conditions, so that good results are achieved.

The inventive parameter optimization with the aid of the reference to the statistical evaluation (see FIG. 1) is a very suitable tool in high-content analysis. Particularly the optimization with respect to the Ŝ-value appears very suitable. This value may not be all too easily handled, but it has become apparent that the Ŝ-minimization will entail also a significant improvement of the Z'-value. The partially very long computing times are somewhat discouraging at first glance. However, these can still be considerably reduced by parallelizing the computation of the object function through subdivision of the data into wells or subwells and by use of a more powerful computer.

The application to the exemplary assays has evidenced a plurality of possible fields of application:
1. The optimization method can be used, subsequent to a modeling of the interaction and a rough presetting of the parameters, for fine adjustment of the latter (see application to the Whatman dataset of the Akt3 assay).
2. The method is further suited for setting the parameters of standard image processing routines on the basis of default parameters, even in cases where no background knowledge on the functionality is available. Thus, the algorithm is useful for parameter optimization of a black box (see application to the $ET_4R$ assay).
3. The newly developed method can also be used for adapting the parameters of an existing model to other—but very similar—test conditions, such as, e.g., other microtitration plates or exposure times (see application to the PV dataset of the Akt3 assay).

What is claimed is:

1. An iterative method for use in high-throughput screening or high-content screening to analyze an effect of a test substance on biological and/or biochemical samples, the method comprising:
  (A) providing at least three biological and/or biochemical samples, each sample comprising:
    (i) cells in a quantity that is substantially on the same order of magnitude across each of the samples and
    (ii) a different and known concentration of the test substance in each of the at least three samples;
  (B) marking the samples with at least one marker selected from the group consisting of: a fluorescent marker, a luminescent marker, and a dye marker;
  (C) exciting the marked samples by illuminating or irradiating the samples to produce luminescence;
  (D) obtaining microscopic images of the illuminated or irradiated samples with a microscope, the microscopic images obtained (i) at a plurality of different excitations, emission wavelengths or different polarizations in the excitation radiation, (ii) in different object planes to obtain information on three-dimensional structures and spatial partial regions, or (iii) at different successive times to obtain information on temporal changes of the sample;
  (E) generating image data for each sample from the microscopic images;
  (F) calculating, from the image data for each sample, the activity value for each sample using an evaluation rule, wherein the evaluation rule comprises at least one methodology selected from the group consisting of: (a) segmentation, (b) object detection, (c) determination of geometric values, (d) brightness values analysis, (e) a texture parameters of the total image analysis, (f) a texture parameters of segments or objects detected in the image analysis, (g) a number of objects analysis, (h) a relative position of objects in relation to each other analysis, (i) a relation of brightness degrees in different measurement channels analysis, (j) a statistical value component derived from any of (a)-(i), (j) a percentage of objects or cells having a specific property analysis, and (k) a percentage of a subset of objects or cells having a specific property analysis, wherein the evaluation rule is dependent on a control parameter value, wherein the control parameter value is a starting control parameter value or a modified control parameter value from step (G), wherein the control parameter value is derived from at least one control parameter selected from the group consisting of: brightness thresholds, value thresholds, position and size of masks for integration or object search, threshold values, and weighting factors, and wherein the activity value for each sample describes the effect of the test substance at each concentration of test substance for each sample, thus yielding a determined activity value for each sample (H) determining a degree of the correspondence between the determined activity values for each sample and a dose/effect curve that represents the interrelation between the sample activity and the dose of the test substance, wherein the curve is based on a known theoretical functional model describing the dependence of a theoretical activity value on the respective concentration of the test substance; and (I) numerically adapting the functional model to the determined activity values to increase the degree of correspondence at each concentration of the test substance by modifying the starting control parameter value or the previously applied modified control parameter value from step (F) to yield a modified control parameter value for use in step (F) and repeating the steps (F) to (G) as long as an abort criterion has not been reached.

2. The method according to claim 1, wherein the cells in each of the samples are cells whose reaction to the test substance is to be examined.

3. The method according to claim 1, wherein the at least three samples are between 3 to 30 samples representing from 3 to 30 different concentrations of test substance.

4. The method according to claim 3, wherein the at least three samples represent from 5 to 15 different concentrations of test substance.

5. The method according to claim 1, wherein the known theoretical functional model comprises the Hill equation.

6. The method according to claim 1, wherein the determining the degree of correspondence comprises determining a normalized average square deviation of the calculated activity values from the adapted functional model.

7. The method according to claim 1, wherein the abort criterion comprises at least one criterion selected from the group consisting of: falling short of a previously determined normalized average square deviation of the calculated activity values, falling short of a previously determined minimum change in the calculated activity values from iteration to iteration, and reaching a maximum number of iterations.

8. The method according to claim 1, wherein the modifying the starting control parameter value or the previously applied modified control parameter value is performed by applying the Nelder/Mead iteration algorithm.

9. The method according to claim 1, wherein, in a multi-stage method, there is first optimized a first group of control parameters until a first abort criterion has been reached, and, subsequently, a second group of control parameters is optimized until a second abort criterion has been reached.

10. The method according to claim 1, further comprising: indicating whether the test substance has a desired magnitude of effect on the cells based on the determined degree of correspondence at each concentration of the test substance.

* * * * *